United States Patent
Nakao

(10) Patent No.: US 6,786,092 B2
(45) Date of Patent: Sep. 7, 2004

(54) MUSCLE PRESSURE MEASURING INSTRUMENT FOR MOUTH CAVITY, ADAPTER FOR MOUTH CAVITY MUSCLE PRESSURE MEASURING INSTRUMENT, AND MOUTH PIECE FOR MOUTH CAVITY MUSCLE PRESSURE MEASURING INSTRUMENT

(76) Inventor: Makoto Nakao, 3-12, Okamoto 3-chome, Setagaya-ku, Tokyo 157-0076 (JP)

( * ) Notice: Subject to any disclaimer, the term of this patent is extended or adjusted under 35 U.S.C. 154(b) by 0 days.

(21) Appl. No.: 10/257,736

(22) PCT Filed: Apr. 17, 2001

(86) PCT No.: PCT/JP01/03266

§ 371 (c)(1),
(2), (4) Date: Oct. 16, 2002

(87) PCT Pub. No.: WO01/78602

PCT Pub. Date: Oct. 25, 2001

(65) Prior Publication Data

US 2003/0163065 A1 Aug. 28, 2003

(51) Int. Cl.$^7$ ............................................... A63B 21/02
(52) U.S. Cl. .................................................... 73/379.03
(58) Field of Search ........................ 73/379.01, 379.02, 73/379.03, 379.04

(56) References Cited

U.S. PATENT DOCUMENTS

| 4,432,376 A | * | 2/1984 | Huszar | ....................... 600/587 |
|---|---|---|---|---|
| 4,631,469 A | | 12/1986 | Tsuboi et al. | .................. 322/42 |
| 5,452,727 A | * | 9/1995 | Tura et al. | .................... 600/590 |
| 5,957,133 A | * | 9/1999 | Hart | ....................... 128/207.14 |

FOREIGN PATENT DOCUMENTS

| DE | 197 05 569 C1 | 9/1998 |
|---|---|---|
| JP | 54-39671 | 3/1979 |
| JP | 57-168635 | 10/1982 |
| JP | 3-98818 | 10/1991 |
| JP | 06-341912 | 12/1994 |
| JP | 9-66048 | 3/1997 |
| JP | 2000-42009 | 2/2000 |

* cited by examiner

*Primary Examiner*—Max Noori
(74) *Attorney, Agent, or Firm*—McCracken & Frank LLP

(57) ABSTRACT

Mouthpieces 12 disposed in a mouth between a lower lip, teeth and gum, for example, are mounted to a force measuring device 11. An outer mouthpiece 16 disposed at the lip side is connected via a connecting shaft 28 to a shaft 26, which is a force measuring portion of the force measuring device 11 while an inner mouthpiece 14 disposed at the side of a tooth row is connected to a main body 34 of the force measuring device 11 via a connecting shaft 22 and a mouthpiece-mounting bracket 38. When the mouthpieces 12 are disposed between the lower lip, teeth and gum and the lips are closed, the outer mouthpiece 16 is pulled by the lip. The force pulling the outer mouthpiece 16 is the lip pressure, and the lip pressure at a rest position and the maximum lip pressure (the pressure of a tongue when the mouthpieces 12 are disposed at the side of a body of tongue) of an examinee are displayed on a display 36 of the force measuring device 11.

19 Claims, 16 Drawing Sheets

MUSCLE PRESSURE MEASURING INSTRUMENT FOR MOUTH CAVITY, ADAPTER FOR MOUTH CAVITY MUSCLE PRESSURE MEASURING INSTRUMENT, AND MOUTH PIECE FOR MOUTH CAVITY MUSCLE PRESSURE MEASURING INSTRUMENT

TECHNICAL FIELD

The present invention relates to a muscle pressure measuring device for a mouth capable of measuring pressure against tooth rows and tooth sockets, which pressure is induced by lips and muscles around an oral cavity or a complex of orbicularis oris and buccinator muscles, and measuring pressure of a tongue; an adapter for the muscle pressure measuring device for a mouth; and mouthpieces for the muscle pressure measuring device for a mouth.

BACKGROUND ART

It is known that soft tissues or muscular tissues around the lips not only have an effect on oral functions but also have close relevance to maintenance and the like of a normal dental arch.

Further, it is known that strong compression on a tooth row by the pressure of muscles around an oral cavity, such as the pressure of the lips, a buccinator muscle, a tongue, or the like, greatly affects implants, odontopathy such as periodontitis, and the treatment using prosthodontics in general dental treatment, and especially orthodontic treatment.

Further, depending on the amount, the pressure of the muscles around the oral cavity, the pressure of the lips, and the pressure of the tongue affect teeth not only during the orthodontic treatment but also retention after the orthodontic treatment, namely, stabilization of the prognosis.

Therefore, when orthodontic treatment is carried out with no regard to the pressure of the muscles around the oral cavity, the pressure of the lips, and the pressure of the tongue, the orthodontic treatment may not be satisfactory. Even if orthodontic treatment has been carried out, the prognosis may not be stable, and regression may be caused.

For this reason, when the courses of treatment are decided in orthodontic diagnosis and before treatment is carried out, it is necessary to study the pressure of the lips, the pressure of the muscles around the oral cavity, and the pressure of the tongue of an examinee who will have teeth-straightening. Further, collecting such data is effective and essential for determining the effects of oral muscle function therapy (M.F.T.).

For example, as a conventional method for measuring the pressure of the lip, a small pressure sensor is inserted into an oral vestibule and disposed between an inner side of the lip and teeth and gum. The pressure of the lip is measured when the lips function in situations of everyday life, such as when the lips are closed, when the lip is at a stable position, and during smiling or drinking fruit juice. However, every measurement is in fact experimental, and thus, this method is not common in daily clinical use.

Another method is also carried out as follows. In order to study the influence of soft tissues on the jaw, the skeletal system of the face, the teeth, the dental arch, and the like, a lip piece is put in the mouth of an examinee and pulled in a fixed direction by an electric motor of a muscle pressure measuring device connected to the lip piece, until the lip piece is pulled out of the lips, and the tractive force (the maximum value) when the lip piece is pulled out of the lips is measured.

However, in the method using the small pressure sensor, the time required to collect data, in other words, the length of the sitting time for which the examinee sits in a chair, becomes long. This places a considerable burden on the examinee.

Further, dispersion of the collected data is significant, and thus the quality of such a set of data is inadequate.

In the method in which the lip piece is pulled by the motor, the device is large and setting time before the test is long, thereby placing a considerable burden on the examinee. In this method, the tractive force when the lip piece is pulled out of the lips is measured. In this case, the tractive force is influenced by not only the strength of the muscles around the oral cavity but also other elements such as the shape, flexibility, or the like of the lips.

Further, not only the lip pressure but also the cheek pressure and the tongue pressure are relevant to the dental arch. Regarding this, the conventional measuring devices for measuring the lip pressure have not been capable of measuring the tongue pressure.

In view of the above-described facts, an object of the present invention is to provide a muscle pressure measuring device for a mouth which can easily and accurately measure, without placing a considerable burden on an examinee sitting in a chair, the pressure on the muscles around the oral cavity such as the pressure of the upper or lower lip, the pressure of the tongue, and the pressure of the cheek, in the mouth (and which can measure the maximum lip pressure, the pressure of the lip at a rest position, the maximum buccinator muscle pressure, the pressure of the buccinator muscle at a rest position, the maximum tongue pressure, the pressure of the tongue at rest, and the pressure of the muscles when they are functioning), an adapter for the muscle pressure measuring device for a mouth, and mouthpieces for the muscle pressure measuring device for a mouth.

MEANS FOR SOLVING THE PROBLEMS

A muscle pressure measuring device according to a first aspect of the invention comprises: a pair of mouthpieces facing each other; and a force measuring device connected to the pair of mouthpiece for measuring force acting on the pair of mouthpieces when the mouthpieces approach each other, the muscle pressure measuring device being capable of measuring at least one of pressure of an upper or lower lip, pressure of a muscle around an oral cavity, pressure of a buccinator muscle, and pressure of a tongue.

The invention according to a second aspect is the muscle pressure measuring device for a mouth of the first aspect, wherein the pair of mouthpieces are curved along a tooth row.

The invention according to a third aspect is the muscle pressure measuring device for a mouth of the first or second aspect, wherein the pair of mouthpieces are removable with respect to the force measuring device.

The invention according to a fourth aspect is the muscle pressure measuring device for a mouth of any one of the first to third aspects, comprising a plurality of mouthpieces of different configurations, which mouthpieces are formed based on an average size of a dental arch of normal occlusion of each age group.

The invention according to a fifth aspect is the muscle pressure measuring device for a mouth of any one of the first to fourth aspects, wherein a recess for avoiding contact with a frenulum of the upper or lower lip is provided in a center of each of the pair of mouthpieces.

The invention according to a sixth aspect is the muscle pressure measuring device for a mouth of any of the first to fifth aspects, wherein a gap between the pair of mouthpieces becomes smaller towards the base of gum when the pair of mouthpiece are disposed along the tooth row.

The invention according to a seventh aspect is the muscle pressure measuring device for a mouth of any of the first to sixth aspects, wherein the mouthpiece comprises an elastic body at at least a portion contacting teeth.

The invention according to an eighth aspect is the muscle pressure measuring device for a mouth of the seventh aspect, wherein the elastic body is detachably provided at the mouthpiece.

The invention according to a ninth aspect is the muscle pressure measuring device for a mouth of any one of the first to eighth aspects, wherein the mouthpiece is formed of metal.

The invention according to a tenth aspect is the muscle pressure measuring device for a mouth of any one of the first to eighth aspects, wherein the mouthpiece is formed of at least one material selected from stainless steel, ceramic, and synthetic resin.

A muscle pressure measuring device for a mouth according to an eleventh aspect comprises: a mouthpiece disposed in a mouth along a tooth row, the mouthpiece comprising at least one fluid chamber which is filled with a fluid and whose wall surfaces are made of a flexible material; and a pressure measuring device which is connected via a tube to the fluid chamber to measure pressure on the fluid inside the fluid chamber.

The invention according to a twelfth aspect is the muscle pressure measuring device for a mouth of the eleventh aspect, wherein a plurality of fluid chambers are provided along the tooth row.

An adapter for a muscle pressure measuring device for a mouth according to a thirteenth aspect comprises: a first mouthpiece which is disposed inside a mouth and includes a first connecting portion connected to a main body of a force measuring device; and a second mouthpiece which is disposed inside the mouth and includes a second connecting portion connected to a force measuring portion of the force measuring device, wherein, when the first connecting portion is connected to the main body and the second connecting portion is connected to the force measuring portion, the first mouthpiece and the second mouthpiece face each other and can measure at least one of pressure of an upper or lower lip, pressure of a muscle around an oral cavity, pressure of a buccinator muscle, and pressure of a tongue.

A mouthpiece for a muscle pressure measuring device for a mouth according to a fourteenth aspect comprises at least one fluid chamber which can be filled with a liquid and whose wall surfaces are formed of a flexible material, the fluid chamber comprising a connecting inlet communicating with the outside of the fluid chamber so that at least one of pressure of an upper or lower lip, pressure of a muscle around an oral cavity, pressure of a buccinator muscle, and pressure of a tongue can be measured.

The invention according to a fifteenth aspect is the mouthpiece for a muscle pressure measuring device for a mouth of the fourteenth aspect, wherein a plurality of fluid chambers are provided along a tooth row.

The invention according to a sixteenth aspect is the muscle pressure measuring device for a mouth of the first aspect, wherein the pair of mouthpieces are formed by an upper mouthpiece abutting the upper lip and a lower mouthpiece abutting the lower lip.

The invention according to a seventeenth aspect is the muscle pressure measuring device for a mouth of the sixteenth aspect, wherein the upper mouthpiece and the lower mouthpiece are removable with respect to the force measuring device.

The invention according to an eighteenth aspect is the muscle pressure measuring device for a mouth of the sixteenth or seventeenth aspect, wherein the upper mouthpiece and the lower mouthpiece are formed of at least one material selected from metals including stainless steel, ceramic, and synthetic resin.

EFFECTS OF THE INVENTION

Next, effects of the muscle pressure measuring device for a mouth according to the first aspect will be described.

In the muscle pressure measuring device for a mouth according to the first aspect, the pair of mouthpieces are disposed in the mouth between, for example, the lip and the tooth row. The pair of mouthpieces are nipped between the lip and the tooth row, and the force (in this case, lip pressure) acting between the pair of mouthpieces is measured by the force measuring device.

The pressure of a tongue can be measured when the pair of mouthpieces are disposed between the tooth row and a body of tongue.

Moreover, the amount of the pressure of a buccinator muscle abutting a group of side teeth (such as a canine tooth, a bicuspid tooth, and a molar tooth) is measurable by disposing the mouthpieces between the cheek and the tooth row.

Further, when the pair of mouthpieces are nipped by the upper and lower lips, closing force of the upper and lower lips can be measured.

Therefore, the muscle pressure measuring device according to the first aspect is effective in that it can easily and accurately measure the muscle pressure of the mouth of an examinee sitting in a chair without placing a considerable burden on the examinee.

Next, effects of the muscle pressure measuring device for a mouth according to the second aspect will be described.

In the muscle pressure measuring device for a mouth according to the second aspect, the pair of mouthpieces are curved along the tooth row. Therefore, for example, when the pair of mouthpieces are disposed between the tooth row and the lip, the gap between the tooth row and the lip can be kept substantially constant, whereby the force (i.e., lip pressure) acting between one and the other of the mouthpiece pair can be accurately measured.

Further, when the pair of mouthpieces are disposed between the tooth row and the body of tongue, the gap therebetween can be kept substantially constant, whereby the lip pressure can be accurately measured.

Next, an effect of the muscle pressure measuring device for a mouth according to the third aspect will be described.

In the muscle pressure measuring device for a mouth according to the third aspect, since the pair of mouthpieces can be dismounted from the muscle pressure measuring device, only the mouthpieces can be easily sterilized.

Next, an effect of the muscle pressure measuring device for a mouth according to the fourth aspect will be described.

The configuration (the size, the curvature, and the like) of the tooth rows varies between adults and children, between the upper jaw and the lower jaw, and between individuals. Thus, accurate measurement can be carried out by preparing in advance a plurality of mouthpieces having different configurations and by selecting and using mouthpieces suited for the tooth row of the examinee.

Next, an effect of the muscle pressure measuring device for a mouth according to the fifth aspect will be described.

In the muscle pressure measuring device for a mouth according to the fifth aspect, the recess for avoiding contact with the frenulum of the upper or lower lip is provided in the center of each of the mouthpieces. Therefore, when the mouthpieces are disposed between the tooth row and the lip, the mouthpieces do not abut the frenulum, and the examinee does not become displeased by the mouthpieces.

Next, an effect of the muscle pressure measuring device for a mouth according to the sixth aspect will be described.

The mouthpieces are structured to measure the muscle pressure under a condition closer to a natural condition in view of the configurations of the tooth row and the lips. Further, the mouthpieces having such a structure can be easily inserted between the lip and the tooth row.

Next, an effect of the muscle pressure measuring device for a mouth according to the seventh aspect will be described.

In the muscle pressure measuring device for a mouth according to the seventh aspect, when the mouthpiece is disposed in the mouth, the mouthpiece contacts the teeth (and the gum) via the elastic body. Therefore, the examinee does not become displeased by the mouthpiece.

Next, an effect of the muscle pressure measuring device for a mouth according to the eighth aspect will be described.

In the muscle pressure measuring device for a mouth according to the eighth aspect, since the elastic body is detachable with respect to the mouthpiece, the mouthpiece and the elastic body can be cleaned and sterilized separately. Further, when the elastic body has deteriorated or is damaged, only the elastic body can be easily replaced with a new elastic body.

Next, an effect of the muscle pressure measuring device for a mouth according to the ninth aspect will be described.

In the muscle pressure measuring device for a mouth according to the ninth aspect, the mouthpieces are formed of metal. Therefore, the mouthpieces hardly deform and are resistant to sterilization at high temperature such as boiling or autoclaving.

Next, an effect of the muscle pressure measuring device for a mouth according to the tenth aspect will be described.

In the muscle pressure measuring device for a mouth according to the tenth aspect, the mouthpieces are formed of at least one material selected from stainless steel, ceramic, and synthetic resin. Thus, the mouthpieces do not rust and are resistant to chemicals and safe to the human body.

Next, effects of the muscle pressure measuring device for a mouth according to the eleventh aspect will be described.

In the muscle pressure measuring device for a mouth according to the eleventh aspect, the mouthpiece is disposed in the mouth between, for example, the lip and the tooth row.

The mouthpiece is nipped by the lip and the tooth row, and the pressure on the fluid inside the fluid chamber is transmitted via the tube to the pressure measuring device and measured. Since the pressure measured by the pressure measuring device corresponds to the force acting on the mouthpiece (in this case, the lip pressure), the lip pressure can be obtained from the measured pressure.

When a pair of mouthpieces are disposed between the tooth row and the body of tongue, the pressure of the tongue can be measured.

Further, the amount of the pressure of the buccinator muscle abutting the side tooth group can be measured by disposing the mouthpiece between the cheek and the tooth row.

Furthermore, the amounts of the lip pressure and the buccinator muscle pressure can be measured at the same time by forming the mouthpiece so that it abuts the entire tooth row.

Moreover, when a pair of mouthpieces are nipped by the upper and lower lips, the closing force of the upper and lower lips can be measured.

Next, an effect of the muscle pressure measuring device for a mouth according to the twelfth aspect will be described.

In the muscle pressure measuring device for a mouth according to the twelfth aspect, since the plurality of fluid chambers are provided along the tooth row, pressure on respective parts of the tooth row can be separately measured.

Further, pressure on each of the teeth can be separately measured by providing a plurality of fluid chambers corresponding to the teeth.

Next, effects of the adapter for a muscle pressure measuring device for a mouth according to the thirteenth aspect will be described.

In the adapter for a muscle pressure measuring device for a mouth according to the thirteenth aspect, the first mouthpiece and the second mouthpiece face each other when the first connecting portion is connected to the main body of the force measuring device and the second connecting portion is connected to the force measuring portion of the force measuring device.

The first mouthpiece and second mouthpiece facing each other are disposed in the mouth between, for example, the lip and the tooth row. The first mouthpiece and the second mouthpiece are nipped between the lip and the tooth row, and the force (in this case, the lip pressure) acting between the first mouthpiece and the second mouthpiece is measured by the force measuring device.

Further, the pressure of the tongue can be measured by disposing the first mouthpiece and the second mouthpiece between the tooth row and the body of tongue.

Furthermore, the amount of the pressure of the buccinator muscle abutting the side tooth group can be measured by disposing the first mouthpiece and the second mouthpiece between the cheek and the tooth row.

Moreover, the closing force of the upper and lower lips can be measured by nipping the pair of mouthpieces between the upper lip and the lower lip.

Next, effects of the mouthpiece for a muscle pressure measuring device for a mouth according to the fourteenth aspect will be described.

In the mouthpiece for a muscle pressure measuring device for a mouth according to the fourteenth aspect, an end of the tube is connected to the connecting inlet in advance, and the other end of the tube is connected to the pressure measuring device. Further, the fluid chamber and the tube are filled with air or a fluid such as water.

When the mouthpiece for a muscle pressure measuring device for a mouth is disposed in the mouth between, for example, the lip and the tooth row, the mouthpiece for a muscle pressure measuring device for a mouth is nipped between the lip and the tooth row, and the pressure on the fluid inside the fluid chamber is transmitted via the tube to the pressure measuring device and measured.

The pressure measured by the pressure measuring device corresponds to the force (in this case, the lip pressure) acting on the mouthpiece for a muscle pressure measuring device for a mouth. Therefore, the lip pressure can be obtained from the measured pressure.

Moreover, the pressure of the tongue can be measured by disposing the mouthpiece for a muscle pressure measuring device for a mouth between the tooth row and the body of tongue.

Further, the amount of the pressure of the buccinator muscle abutting the side tooth group can be measured by disposing the mouthpiece for a muscle pressure measuring device for a mouth between the cheek and the tooth row.

Furthermore, the amounts of the lip pressure and the buccinator muscle pressure can be measured at the same time by forming the mouthpiece for a muscle pressure measuring device for a mouth so that it abuts the entire tooth row.

Next, effects of the mouthpiece for a muscle pressure measuring device for a mouth according to the fifteenth aspect will be described.

In the mouthpiece for a muscle pressure measuring device for a mouth according to the fifteenth aspect, since a plurality of fluid chambers are provided along the tooth row, pressure on respective parts of the tooth row can be separately measured.

Further, pressure on each of the teeth can be separately measured by providing a plurality of fluid chambers corresponding to the teeth.

Next, an effect of the muscle pressure measuring device for a mouth according to the sixteenth aspect will be described.

In the muscle pressure measuring device for a mouth according to the sixteenth aspect, the amount of the closing force of the upper and lower lips can be measured by closing the upper lip and the lower lip with the upper mouthpiece of the mouthpiece pair abutting the upper lip and the lower mouthpiece abutting the lower lip.

Next, an effect of the muscle pressure measuring device for a mouth according to the seventeenth aspect will be described.

In the muscle pressure measuring device for a mouth according to the seventeenth aspect, since the upper mouthpiece and the lower mouthpiece can be dismounted from the muscle pressure measuring device, only the mouthpieces can be easily sterilized.

Next, an effect of the muscle pressure measuring device for a mouth according to the eighteenth aspect will be described.

Since the upper mouthpiece and the lower mouthpiece are formed of metal, the mouthpieces hardly deform and are resistant to sterilization at high temperature such as boiling or autoclaving. When the mouthpieces are formed of at least one material selected from stainless steel, ceramic, and synthetic resin, the mouthpieces do not rust and are resistant to chemicals and safe to the human body.

EMBODIMENTS

[First Embodiment]

Hereinafter, a muscle pressure measuring device 10 for a mouth according to a first embodiment of the present invention will be described with reference to the drawings.

Figure 1:
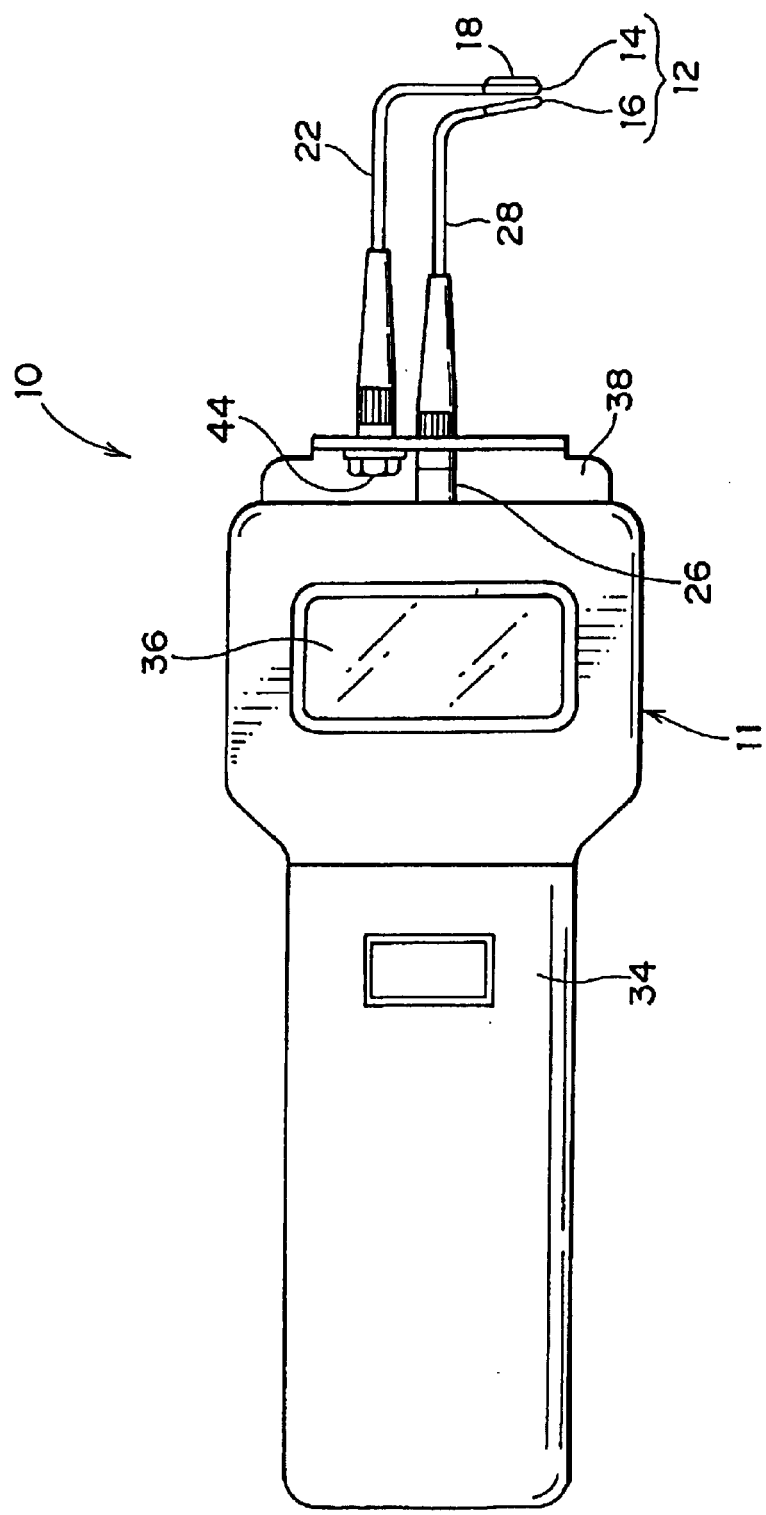
FIG. 1 is an elevation of a muscle pressure measuring device for a mouth according to a first embodiment of the present invention.

As shown in FIG. 1, the muscle pressure measuring device 10 for a mouth includes mouthpieces 12 to be disposed in the mouth of an examinee, and a force measuring device 11.

Figure 2:
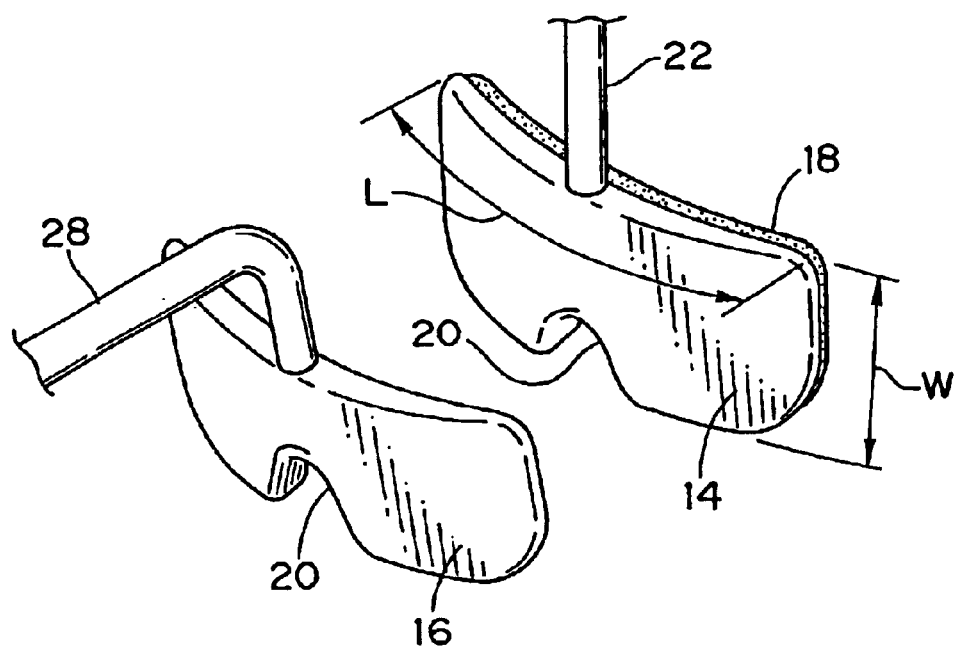
FIG. 2 is a perspective view of mouthpieces.

As shown in FIG. 2, the mouthpieces 12 include an inner mouthpiece 14 and an outer mouthpiece 16.

The inner mouthpiece 14 and the outer mouthpiece 16 are each formed in an elongated plate shape and curved in a longitudinal direction thereof.

The inner mouthpiece 14 and the outer mouthpiece 16 of the present embodiment have such a width (W) that they are accommodated in the oral vestibule between an inner side of an upper lip and front teeth and gum of an upper jaw, or between an inner side of a lower lip and front teeth and gum of a lower jaw.

Figure 3:
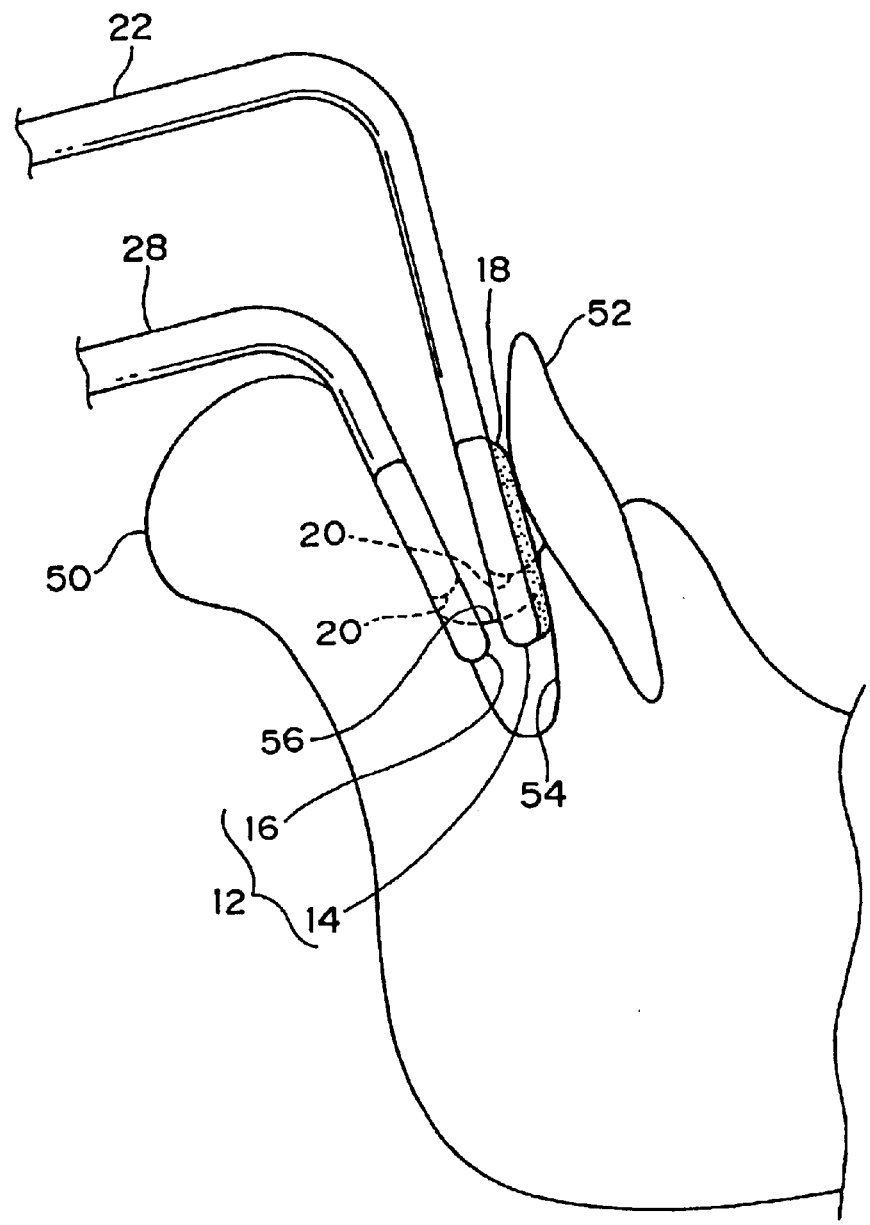
FIG. 3 is a side view showing a state in which the pressure of a lip is being measured using the muscle pressure measuring device for a mouth according to the first embodiment of the present invention.

As shown in FIG. 3, the inner mouthpiece 14 is disposed on a tooth row in the oral vestibule, while the outer mouthpiece 16 is disposed on the lip in the oral vestibule.

The inner mouthpieces 14 and 16 are curved so as to conform to the arch of the tooth row. The outer mouthpiece 16 is curved in the shape of a circular arc having a radius of curvature slightly larger than that of the inner mouthpiece 14, and smoothly contacts the inner side of the lip.

The inner mouthpiece 14 and the outer mouthpiece 16 are often formed of a metallic material, such as stainless steel, in view of sterilization (by boiling, autoclaving, alcohol, or the like) and durability. The inner mouthpiece 14 and the outer mouthpiece 16 of the present embodiment are formed of stainless steel.

Figure 4:
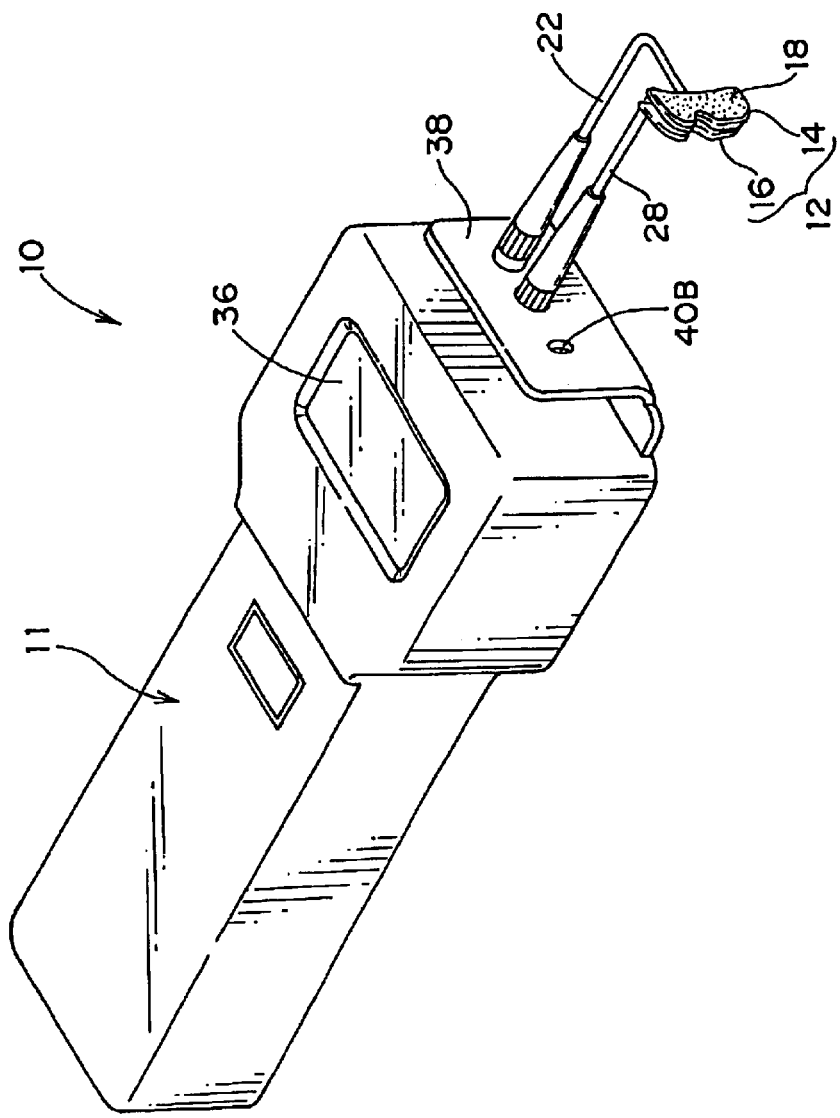
FIG. 4 is a perspective view of the muscle pressure measuring device for a mouth according to the first embodiment of the present invention.

As shown in FIGS. 3 and 4, a sheet-shaped cushion 18 of an elastic body is attached to an inner surface of the inner mouthpiece 14 of the present embodiment with an adhesive or the like.

Figure 5:
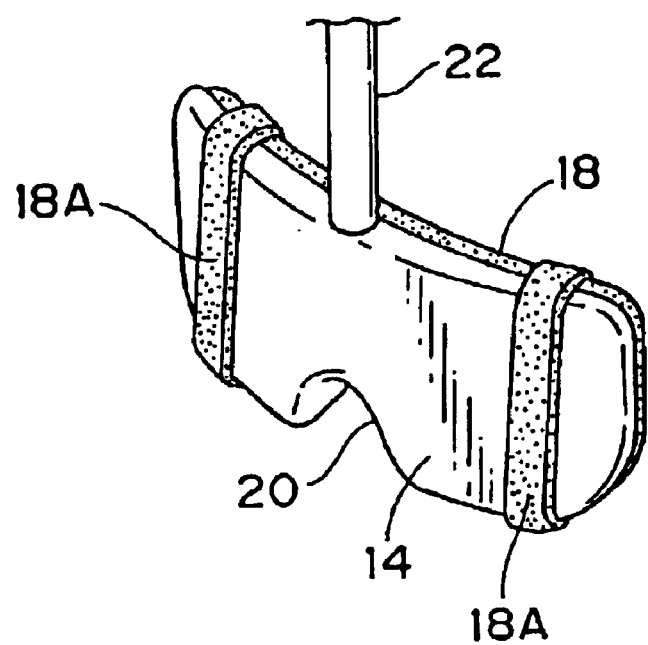
FIG. 5 is a perspective view of another example of a cushion.

As shown in FIG. 5, the cushion 18 may have strips 18A mounted to ends of the inner mouthpiece 14 so that the cushion 18 is detachably mounted to the inner mouthpiece 14.

Further, in view of sterilization and the like, the material for the cushion 18 is often soft synthetic resin, rubber (such as silicone rubber), or the like, which has excellent resistance to heat, chemicals, and the like.

As shown in FIGS. 2 and 3, in order to avoid contact with a frenulum of the lip, a substantially V-shaped notch 20 is formed in the center of an edge of each of the inner mouthpiece 14, the cushion 18, and the outer mouthpiece 16, which center corresponds to the base of the gum.

As shown in FIG. 1, a connecting shaft 22, which connects to a mouthpiece-mounting bracket 38 of the force measuring device 11 to be described later, is integrally connected to the inner mouthpiece 14. As well as the inner mouthpiece 14, the connecting shaft 22 is formed of stainless steel.

Figure 6:
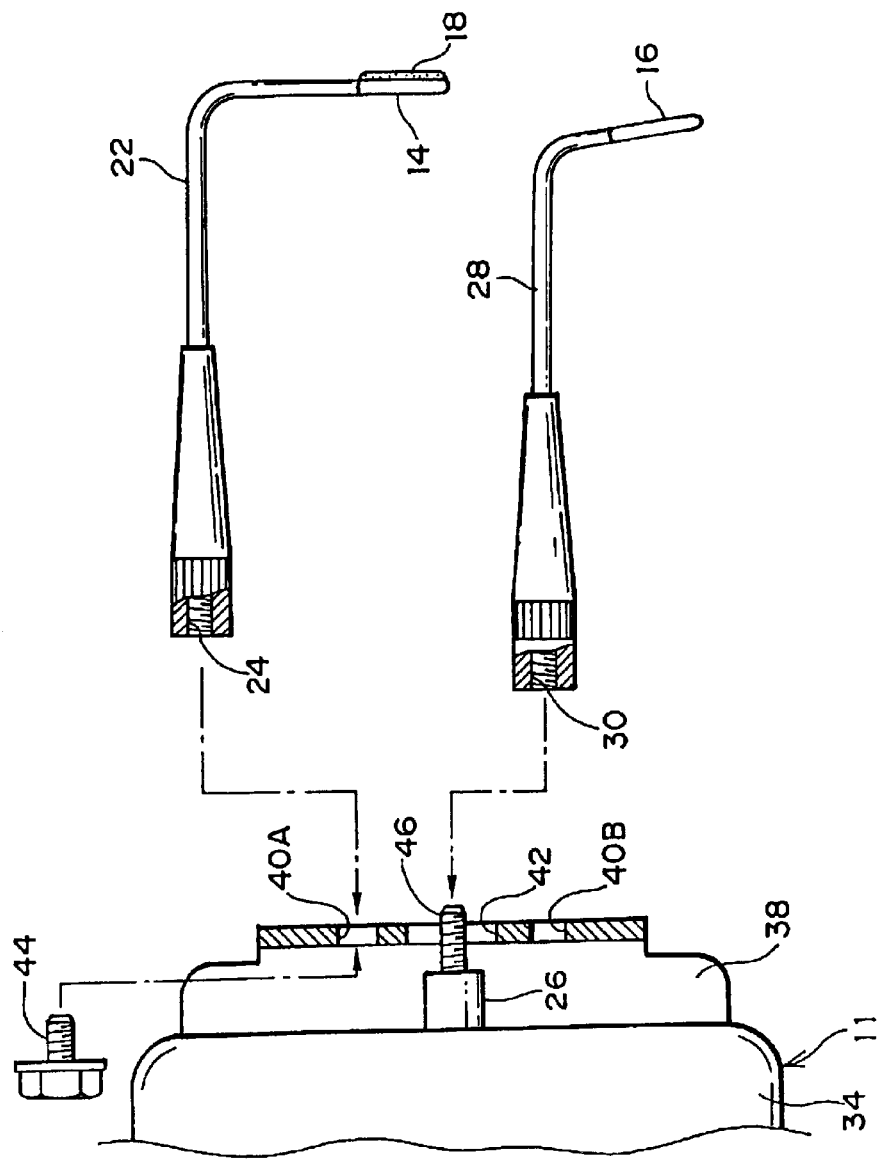
FIG. 6 is an elevational view showing a portion at which the mouthpieces are connected to the muscle pressure measuring device.

As shown in FIGS. 2 and 6, the connecting shaft 22 extends from a central portion of the inner mouthpiece 14 in a direction orthogonal to the longitudinal direction thereof, is bent at a substantially right angle, and extends in a radially outward direction of the curved portion of the inner mouthpiece 14. The end portion of the connecting shaft 22 is thick, and an internal thread 24 is formed at the leading end thereof.

A connecting shaft 28, which connects to a shaft 26 of the force measuring device 11 to be described later, is integrally connected to the outer mouthpiece 16. As well as the outer mouthpiece 16, the connecting shaft 28 is formed of stainless steel.

The connecting shaft 28 extends from a central portion of the outer mouthpiece 16 in a direction orthogonal to the longitudinal direction thereof, is bent at an angle slightly larger than 90°, and extends in a radially outward direction of the curved portion of the outer mouthpiece 16. The end portion of the connecting shaft 28 is thick, and an internal thread 30 is formed at the leading end thereof.

The force measuring device 11 of the present embodiment is, for example, a digital force measuring device with a strain gauge or the like. As shown in FIG. 1, the amount of force acting in an axial direction of the shaft 26 is digitally displayed on a display 36 of a main body 34.

The force measuring device 11 has functions of storing and displaying the maximum value of the measured force.

Since the force measuring device 11 is known and commercially available from A & D Co., LTD. or IMADA, INC., for example, the detailed description thereof is omitted.

Further, the force measuring device 11 is capable of measuring both tensile force and compressive force acting on the shaft 26.

The mouthpiece-mounting bracket 38 is mounted to the main body 34 of the force measuring device 11 via unillustrated screws.

As shown in FIG. 6, mounting holes 40A and 40B through which the connecting shaft 22 of the inner mouthpiece 14 is mounted to the mouthpiece-mounting bracket 38, and a relief hole 42 into which the connecting shaft 28 of the outer mouthpiece 16 is inserted are formed in the mouthpiece-mounting bracket 38.

The inner mouthpiece 14 is connected via the connecting shaft 22 and the mouthpiece-mounting bracket 38 to the main body 34 of the force measuring device 11 by fastening a bolt 44 which is inserted through the mounting hole 40A of the mouthpiece-mounting bracket 38 into the internal thread 24 formed at the connecting shaft 22 of the inner mouthpiece 14.

An external thread 46 is formed at the end of the shaft 26 of the force measuring device 11. The outer mouthpiece 16 is connected via the connecting shaft 28 to the shaft 26 by screwing the external thread 46 into an internal thread 30 formed at the connecting shaft 28 of the outer mouthpiece 16.

Figure 7:
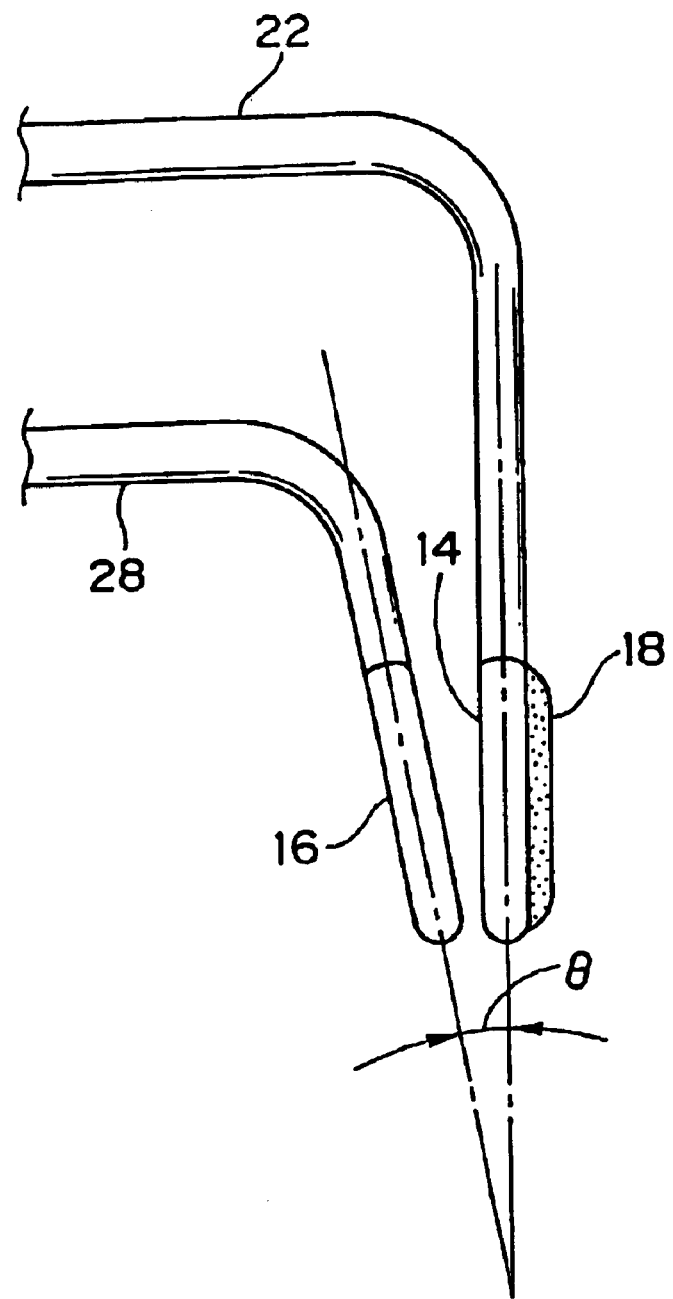
FIG. 7 is a side view of the mouthpieces.

As shown in FIG. 7, since a small gap is provided between the inner mouthpiece 14 and the outer mouthpiece 16 when they are connected to the force measuring device 11, measurement can be performed providing a condition closer to a natural condition. Further, a small angle θ is formed between the inner mouthpiece 14 and the outer mouthpiece 16, and the gap between the mouthpieces at the gum base side is smaller than the gap between the mouthpieces at the connecting shaft side so that it becomes easy to insert the mouthpieces between the lip and the teeth.

Next, usage of the muscle pressure measuring device 10 for a mouth of the present embodiment will be described.

FIG. 3 is a side view showing a state in which the pressure of the lower lip is being measured using the muscle pressure measuring device 10 for a mouth.

(1) First, the mouthpieces 12 are disposed in the oral vestibule between a lower lip 50 and several front teeth 52 and gum 54.

At this time, the inner mouthpiece 14 is somewhat pressed against the teeth 52 (and the gum 54) and secured thereto. If the inner mouthpiece 14 is away from the teeth 52 (and the gum 54), accurate measurement cannot be carried out.

(2) When the examinee closes and strains his/her lips in this state, the inner mouthpiece 14 and the outer mouthpiece 16 are nipped between the lower lip 50 and the teeth 52 and the gum 54, whereby the shaft 26 of the force measuring device 11 is pulled.

The force acting on the shaft 26 is the pressure of the lower lip 50. The amount of the force acting on the shaft 26, namely, the amount of the lip pressure, is digitally displayed (for example, in grams) on the display 36.

Further, since the notches 20 are provided at the inner mouthpiece 14 and the outer mouthpiece 16 to avoid contact with a frenulum 56 of the lip, when the lips are closed and strained, the inner mouthpiece 134 and the outer 5 mouthpiece 16 do not abut the frenulum 56 of the lip and thus do not displease the examinee.

Furthermore, when the inner mouthpiece 14 and the outer mouthpiece 16 are disposed in the oral vestibule, the metallic inner mouthpiece 14 abuts the teeth 52 and the gum 54 via the cushion 18. Therefore, the examinee does not become displeased by the mouthpieces 12.

(3) Although not shown, the pressure of the upper lip can be measured by changing the orientation of the muscle pressure measuring device 10 for a mouth so that the mouthpieces 12 shown in FIG. 3 are turned upside down and disposing the mouthpieces 12 between the upper lip and teeth and gum.

(4) The length L of the inner mouthpiece 14 and the outer mouthpiece 16 along the tooth row (see FIG. 2) is 20 mm to about 30 cm (and preferably about 25 mm) for the upper jaw and about 25 mm for the lower jaw.

(5) Plural types of the inner mouthpiece 14 and outer mouthpiece 16 having different shapes and sizes such as different radii of curvature and different lengths may be prepared in advance, and the inner mouthpiece 14 and the outer mouthpiece 16 which conform to the configuration of the tooth row of the examinee may be mounted to the force measuring device 11. This enables more accurate measurement of the lip pressure.

(6) Moreover, the inner mouthpiece 14 and the outer mouthpiece 16 which have been used can be dismounted from the force measuring device 11 and sterilized. Therefore, the inner mouthpiece 14 and the outer mouthpiece 16 are sanitary.

Mouthpieces for measuring the pressure of a buccinator muscle abutting the group of the side teeth (such as a canine tooth, a bicuspid tooth, and a molar tooth) may be prepared separately. These mouthpieces will be described in detail in a sixth embodiment.

Further, although the inner mouthpiece 14 and the outer mouthpiece 16 are formed of stainless steel in the present embodiment, they may be formed of other metal and coated with synthetic resin such as Teflon. Furthermore, the inner mouthpiece 14 and the outer mouthpiece 16 may be formed of a material other than metal, such as ceramic, hard synthetic resin, or the like.

In the present embodiment, the connecting shafts 22 and 28 are screwed on the force measuring device 11. However, the connecting shafts 22 and 28 may be detachably connected to the force measuring device 11 via one-touch joints.

The mouthpieces 12 are manufactured so as to be sterilized. However, in order to save a great deal of trouble sterilizing, the entire mouthpieces 12 may be covered with a bag-like cover formed of vinyl or the like, and the cover may be replaced for each measurement (every examinee).

[Second Embodiment]

A muscle pressure measuring device 60 for a mouth according to a second embodiment of the present invention will be described.

Components of the device of the present second embodiment which are similar to those of the device of the first embodiment are designated by the same reference numerals, and detailed description thereof will be omitted.

The muscle pressure measuring device 60 for a mouth of the present embodiment measures pressure of the body of tongue on the tooth row, namely, pressure of a tongue.

Figure 8:
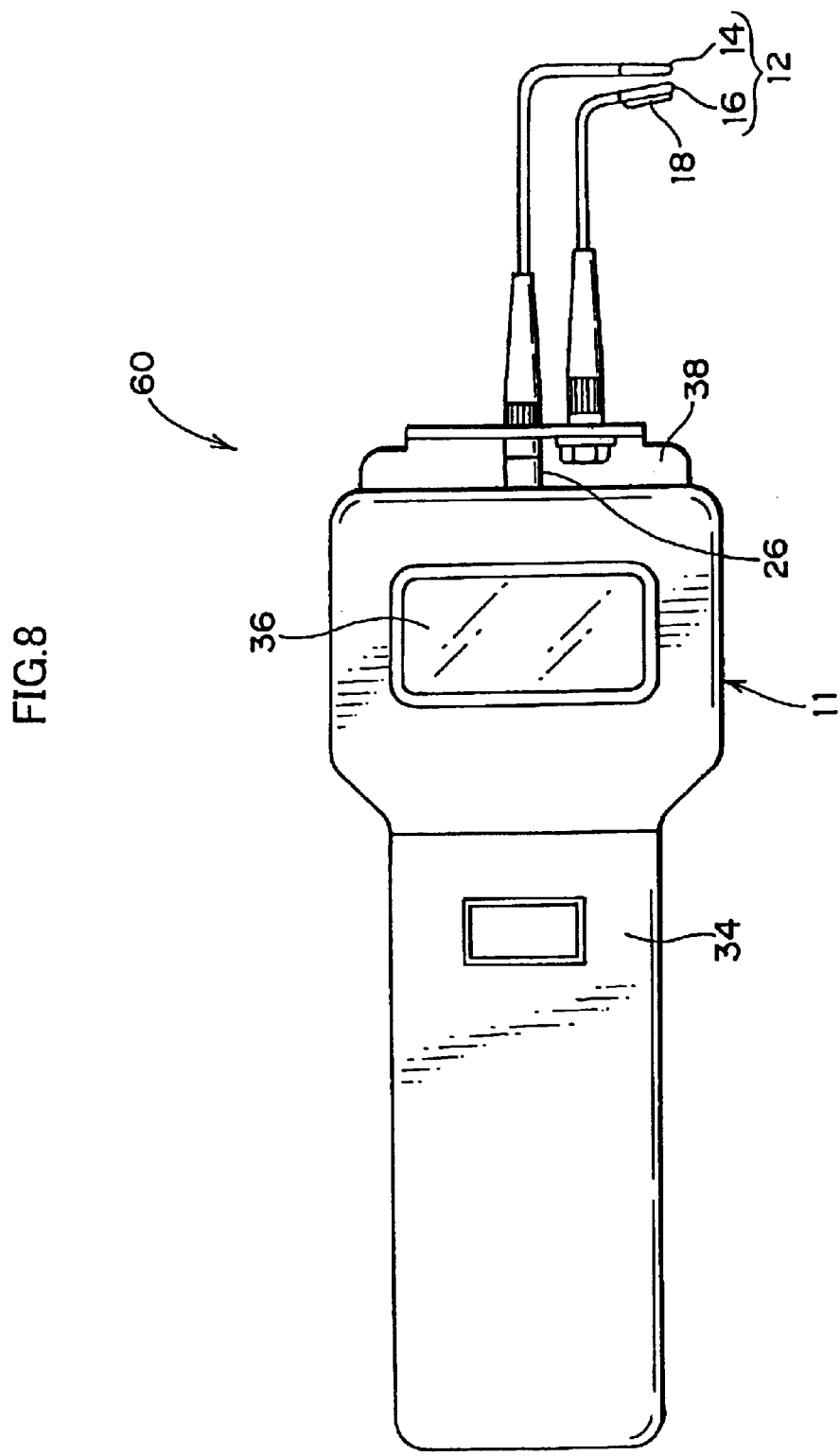
FIG. 8 is an elevational view of a muscle pressure measuring device for a mouth according to a second embodiment of the present invention.

In the present embodiment, as shown in FIG. 8, the inner mouthpiece 14 is connected to the shaft 26 of the force measuring device 11, and the outer mouthpiece 16 is connected to the mouthpiece-mounting bracket 38.

Further, in the present embodiment, the cushion 18 is attached to the outer mouthpiece 16.

Next, usage of the muscle pressure measuring device 60 for a mouth of the present embodiment will be described.

Figure 9:
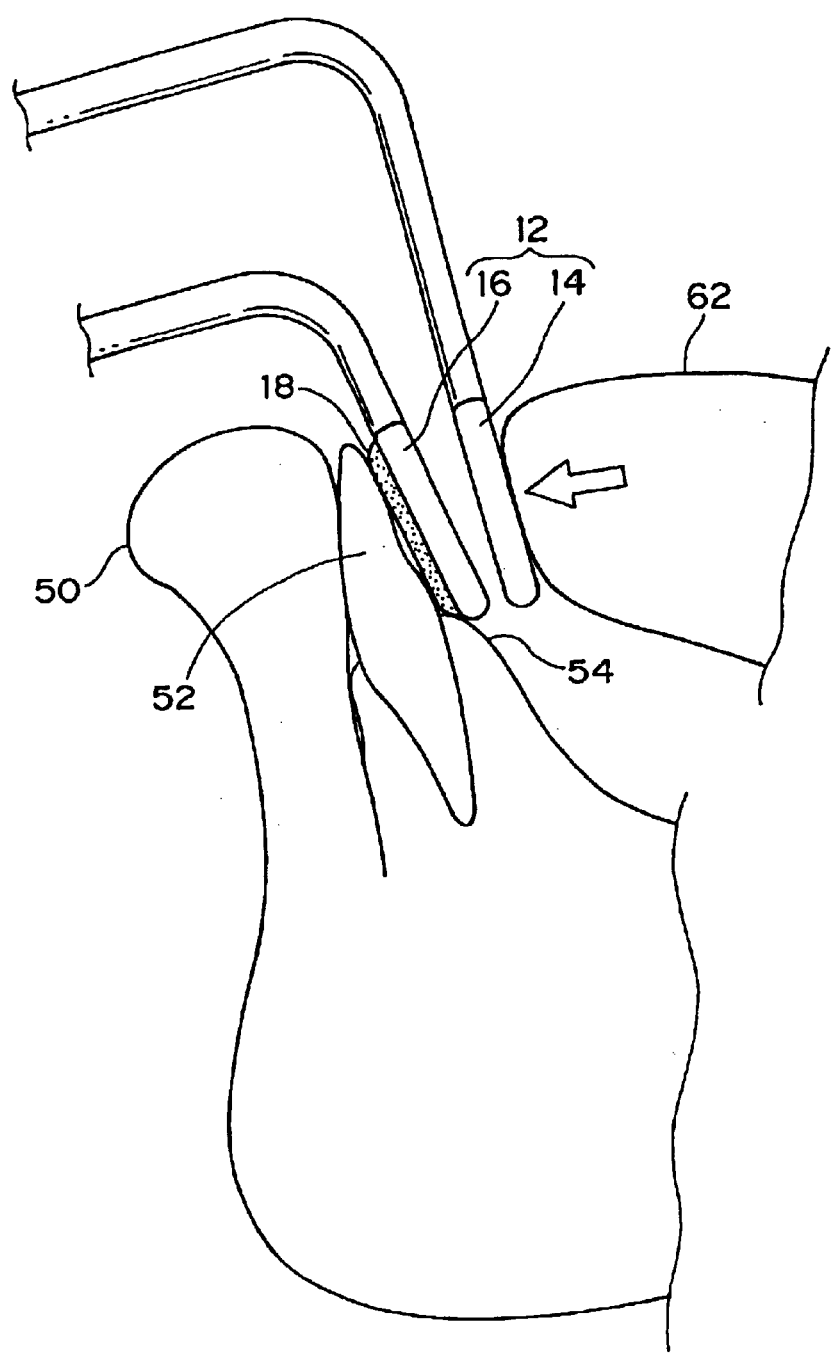
FIG. 9 is a side view showing a state in which the pressure of a tongue is being measured using the muscle pressure measuring device for a mouth according to the second embodiment of the present invention.

FIG. 9 is a side view showing a state in which the pressure of the tongue is being measured using the muscle pressure measuring device 60 for a mouth.

(1) First, the mouthpieces 12 are disposed in the mouth between a body of tongue 62 and the teeth 52 and the gum 54.

(2) When the examinee closes his/her lips in this state, the inner mouthpiece 14 and the outer mouthpiece 16 are nipped between the body of tongue 62 and the teeth 52 and the gum 54, whereby the shaft 26 of the force measuring device 11 is pressed.

The force acting on the shaft 26 is the pressure of the tongue. The amount of the force acting on the shaft 26, namely, the amount of the tongue pressure, is digitally displayed on the display 36.

When the inner mouthpiece 14 and the outer mouthpiece 16 are disposed in the mouth, the metallic outer mouthpiece 16 abuts the teeth 52 and the gum 54 via the cushion 18. Therefore, the examinee does not become displeased by the mouthpieces 12.

[Third Embodiment]

A muscle pressure measuring device 70 for a mouth according to a third embodiment of the present invention will be described.

Figure 10:
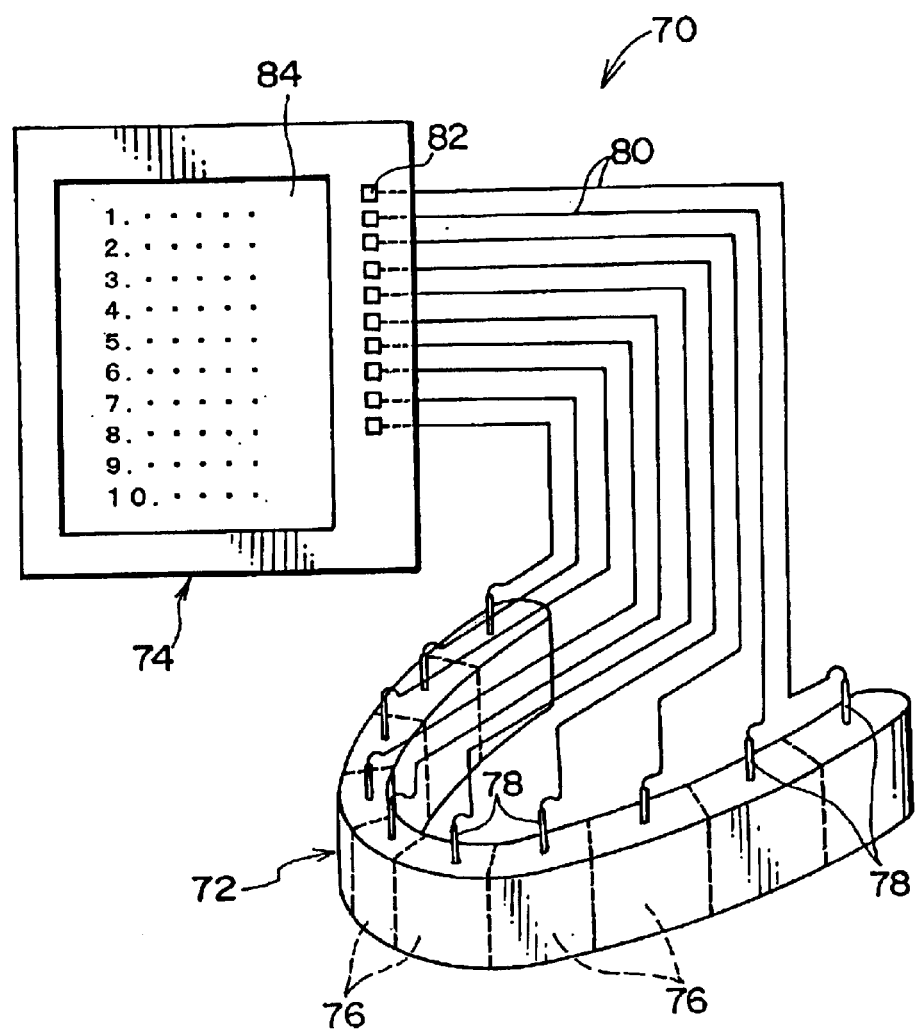
FIG. 10 is a perspective view of a muscle pressure measuring device for a mouth according to a third embodiment of the present invention.

As shown in FIG. 10, the muscle pressure measuring device 70 for a mouth of the present embodiment includes a mouthpiece 72 and a pressure measuring device 74.

The mouthpiece 72 is formed by connecting square or rectangular fluid chambers 76 of a fixed thickness along the tooth row (in the present embodiment, all the teeth ranging from front teeth to molar teeth).

The mouthpiece 72 is formed of thin and flexible synthetic resin or rubber. Wall surfaces of the fluid chamber 76 are easily deformable.

A connecting inlet 78 is formed integrally with each fluid chamber 76.

An end of a tube 80 is detachably connected to the connecting inlet 78.

The other end of the tube 80 is connected to a pressure sensor 82 of the pressure measuring device 74.

A display 84 for displaying the pressure on the pressure sensor 82 is provided at the pressure measuring device 74.

Next, usage of the muscle pressure measuring device 70 for a mouth of the present embodiment will be described.

Figure 11:
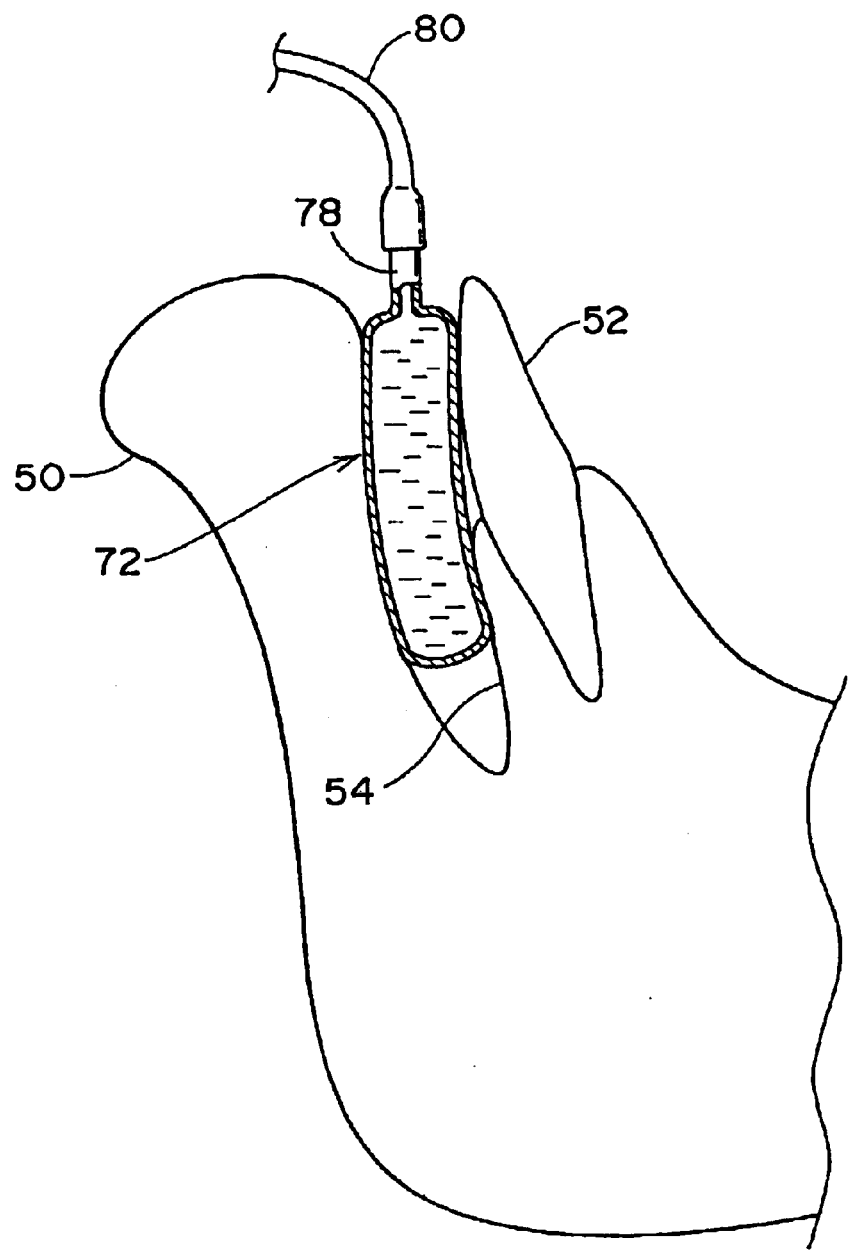
FIG. 11 is a side view showing a state in which the pressure of the lip is being measured using the muscle pressure measuring device for a mouth according to the third embodiment of the present invention.

FIG. 11 is a side view showing a state in which the pressure of the lip is being measured using the muscle pressure measuring device 70 for a mouth.

(1) First, the mouthpiece 72 is disposed in the oral vestibule between the lower lip 50 and cheeks and the tooth row (the teeth 52 and the gum 54) in the lower jaw. Each of the fluid chambers 76 of the mouthpiece 72 and each of the tubes 80 are filled in advance with a certain amount of air or a liquid using an injector, which liquid does not adversely affect the human body, such as distilled water.

(2) When the examinee closes and strains his/her lips in this state, the mouthpiece 72 is nipped between the lower lip 50 and the cheeks and the tooth row in the lower jaw, whereby the force acting on each of the fluid chambers 76 is transmitted via the tube 80 to the pressure sensor 82.

The amount of the force acting on each of the fluid chambers 76, namely, the amounts of the lip pressure and the pressure of buccinator muscles abutting groups of side teeth (such as canine teeth, bicuspid teeth, and molar teeth) are digitally displayed (for example, in MPa) on the display 84.

Further, by making one fluid chamber 76 correspond to one tooth, the pressure on each tooth can be separately measured using the mouthpiece 72.

Since the mouthpiece 72 of the present embodiment is formed by molding flexible synthetic resin or the like, the mouthpiece 72 does not displease the examinee when disposed in the mouth.

(3) Although not shown, the amount of the pressure of the upper lip and the amounts of the pressure of the buccinator muscles abutting groups of side teeth in the upper jaw can be measured by disposing the mouthpiece 72 between the upper lip and the tooth row in the upper jaw.

(4) Further, the mouthpieces 72 of various sizes (for example, the mouthpieces 72 for adults, children, and others) may be prepared. The size of the fluid chamber 76 is changed if necessary.

The lip pressure can be measured more accurately by using the mouthpiece 72 having the right size for the tooth row of the examinee.

Since the mouthpiece 72 of the present embodiment is flexible, the mouthpiece 72 only needs to be slightly curved as shown in FIG. 10 (or does not need to be curved in some cases).

Even if the curve of the mouthpiece 72 does not correspond to the curve of the tooth row of the examinee, the flexible mouthpiece 72 conforms to the shape of the tooth row when disposed in the mouth. Therefore, the mouthpiece 72 causes no problems in measurement.

Further, when the mouthpiece 72 is a molded article of synthetic resin, the mouthpiece 72 can be produced in large quantities at low cost. Thus, the mouthpiece 72 can be thrown away after single use, and the trouble of sterilization can be relieved.

Of course, the lip pressure can be measured by disposing the mouthpiece 72 between the body of tongue 62 and the teeth 52.

In the present embodiment, the lip pressure and the tongue pressure can be measured at the same time by using two mouthpieces 72. In this case, a pair of the mouthpieces 72 may be connected to each other with the tooth row being interposed therebetween.

[Fourth Embodiment]

A muscle pressure measuring device 90 for a mouth according to a fourth embodiment of the present invention will be described.

Figure 12:
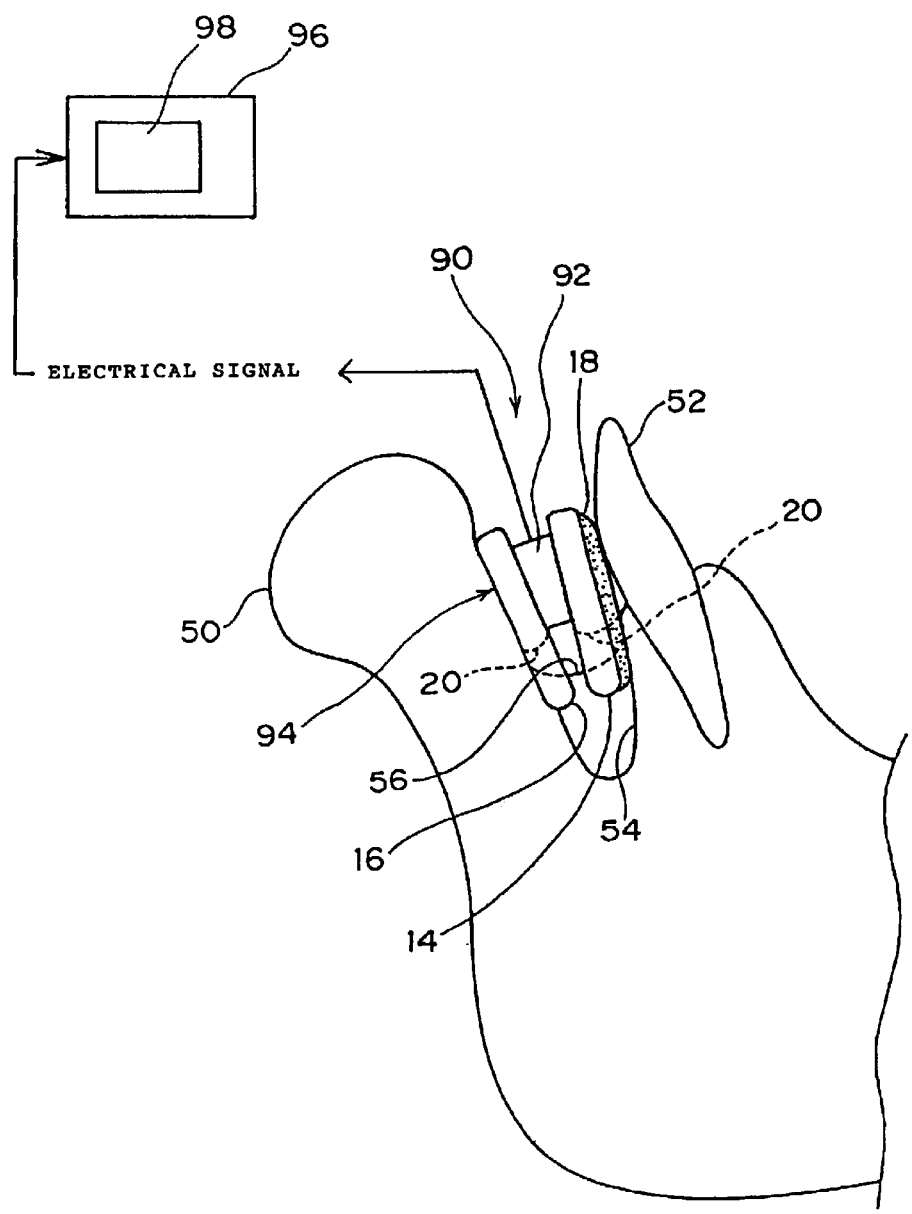
FIG. 12 is a side view showing a state in which the pressure of the lip is being measured using a muscle pressure measuring device for a mouth according to a fourth embodiment of the present invention.

As shown in FIG. 12, the muscle pressure measuring device 90 for a mouth of the present embodiment includes mouthpieces 94 formed by the inner mouthpiece 14 and the outer mouthpiece 16 with a small pressure sensor 92 being provided therebetween, and a display unit 96 for displaying the amount of force acting between the inner mouthpiece 14 and the outer mouthpiece 16.

The pressure sensor 92 outputs to the display unit 96 an electrical signal corresponding to the amount of the pressure, such that the amount of the force is displayed on a display 98 of the display unit 96.

Usage of the mouthpieces 94 is the same as that of the mouthpieces 12 and the like. The lip pressure can be measured by disposing the mouthpieces 94 between the lip and the teeth and the gum. The tongue pressure can be measured by disposing the mouthpieces 94 between the body of tongue and the teeth and the gum. Further, the pressure of the buccinator muscle abutting the side tooth group can also be measured by disposing the mouthpieces 94 on the outer side of the side tooth group. (In this case, the mouthpieces 94 configured to conform to the curve of a row of the side teeth are used.)

[Fifth Embodiment]

A muscle pressure measuring device 100 for a mouth according to a fifth embodiment of the present invention will be described.

Figure 13:
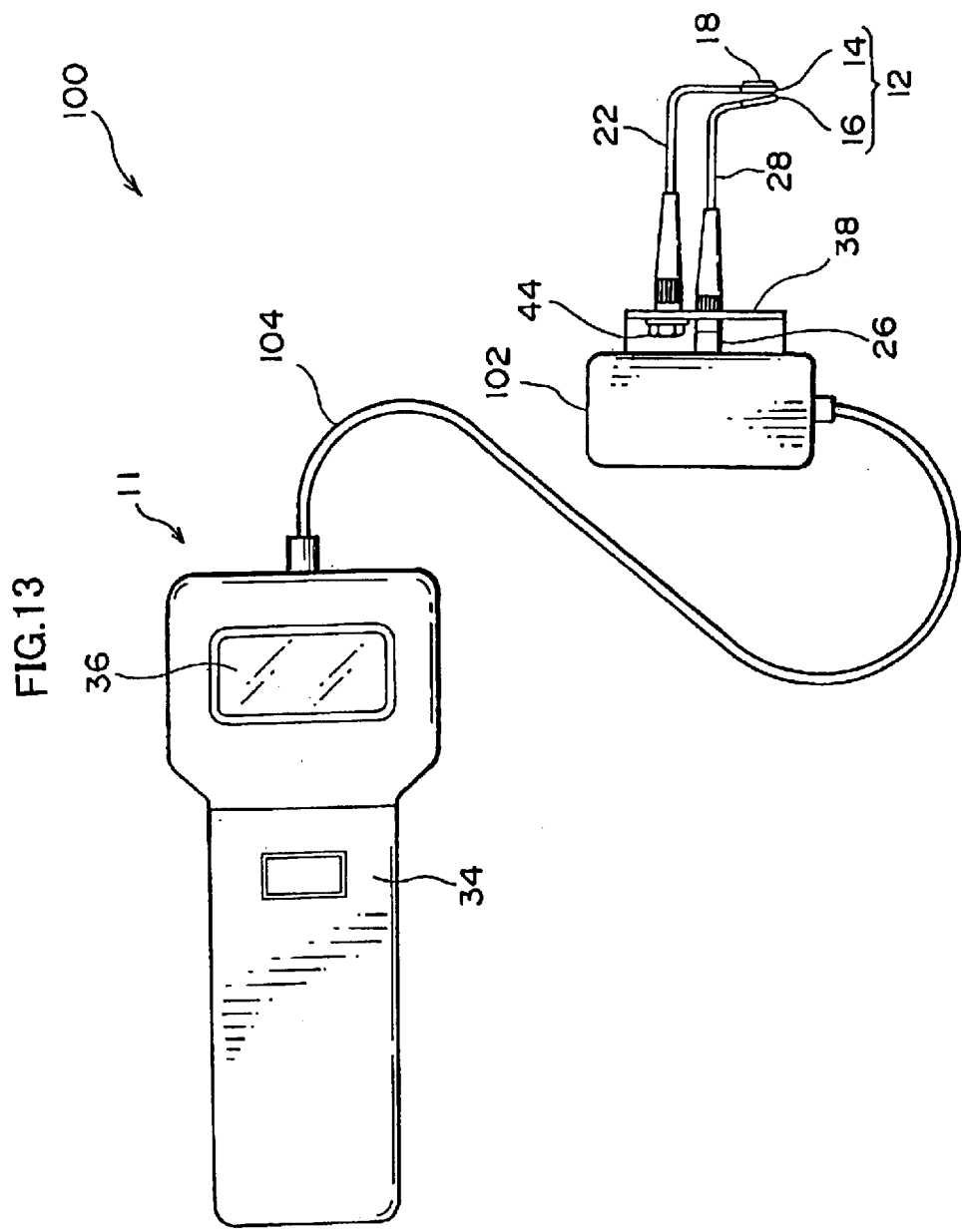
FIG. 13 is an elevational view of a muscle pressure measuring device for a mouth according to a fifth embodiment of the present invention.

As shown in FIG. 13, the muscle pressure measuring device 100 for a mouth of the present embodiment is a modified example of the muscle pressure measuring device 10 for a mouth according to the first embodiment. Components of the device of the present embodiment which are similar to those of the device of the first embodiment are designated by the same reference numerals, and detailed description thereof will be omitted.

As shown in FIG. 13, in the force measuring device 11 of the present embodiment, a sensor 102 is separated from the main body 34 including the display 36, and the main body 34 is connected to the sensor 102 via a cable 104. As the examples of the force measuring device 11 in which the sensor 102 is separated from the main body 34, separate-type digital force gauge sensors of DPX-DPU series and the like available from IMADA, INC. are applicable.

In the present embodiment, the mouthpieces 12 are mounted to the sensor 102. Usage of the muscle pressure measuring device 100 for a mouth is the same as that of the muscle pressure measuring device 10 for a mouth of the first embodiment.

In the muscle pressure measuring device 100 for a mouth of the present embodiment, the main body 34 is connected to the sensor 102 via the cable 104. However, data of measured pressure obtained at the sensor 102 can be transmitted to the main body 34 by wireless via radio waves or using infrared light.

Further, in the first embodiment, the inner mouthpiece 14 and the outer mouthpiece 16 are connected to the force measuring device 11 via the connecting shafts 22 and 28, respectively. However, in place of the connecting shafts 22 and 28, the inner mouthpiece 14 and the outer mouthpiece 16 may be mechanically connected to the force measuring device 11 by wire cables or the like which transmit force.

[Sixth Embodiment]

A muscle pressure measuring device 110 for a mouth according to a sixth embodiment of the present invention will be described with reference to FIGS. 14 and 15. Components of the device of the present embodiment which are similar to those of the devices of the above-described embodiments are designated by the same reference numerals, and detailed description thereof will be omitted.

Figure 14:
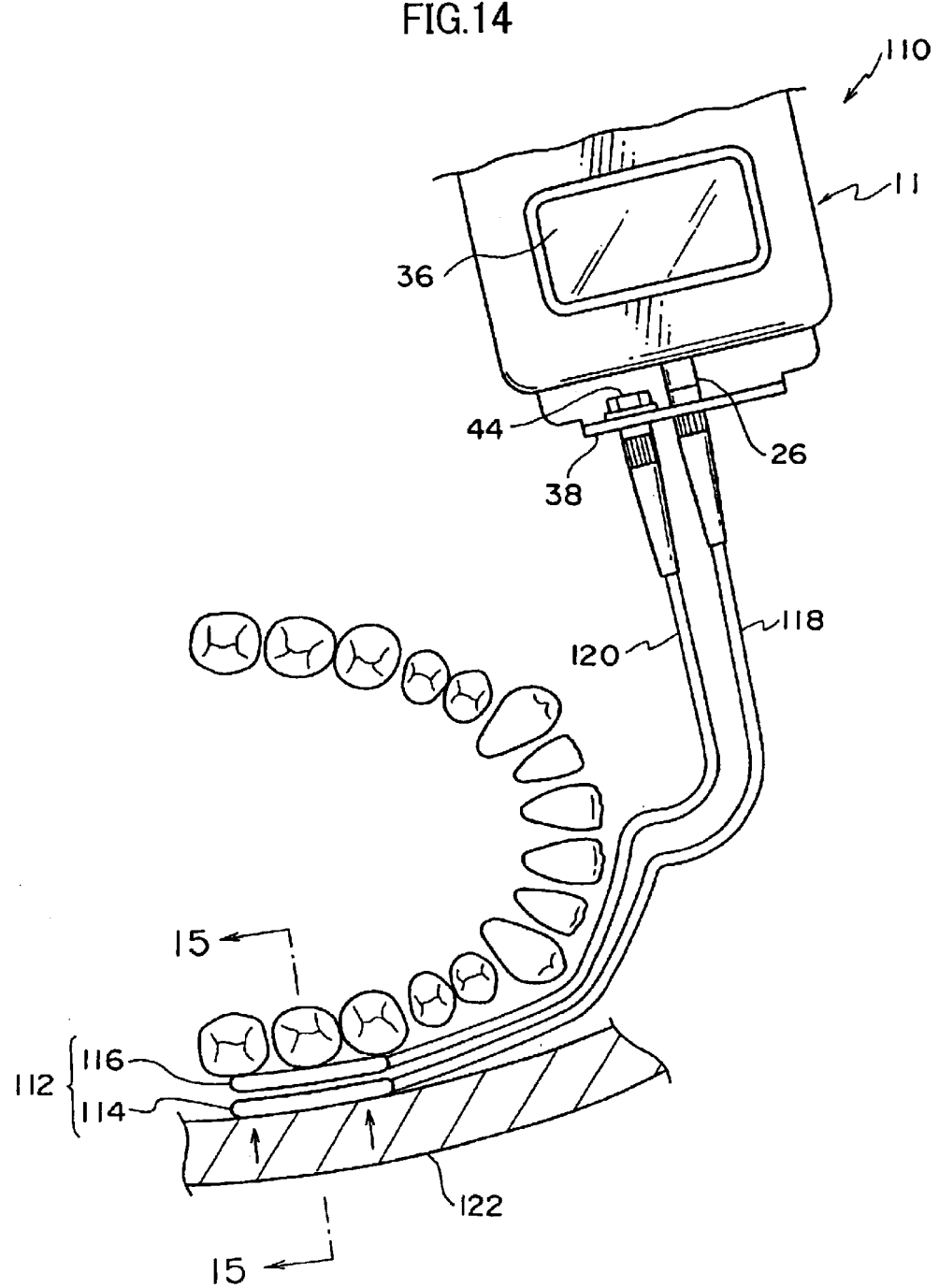
FIG. 14 is a plan view showing a state in which the pressure of a buccinator muscle is being measured using a muscle pressure measuring device for a mouth according to a sixth embodiment of the present invention.

FIG. 14 is a plan view showing a state in which the pressure of a buccinator muscle is being measured using the muscle pressure measuring device 110 for a mouth. FIG. 15 is a cross-sectional view taken along a direction orthogonal to the tooth row (i.e., cross-sectional view taken along line 15—15 of FIG. 14), showing a state in which the pressure of the buccinator muscle is being measured using the muscle pressure measuring device 110 for a mouth.

Figure 15:
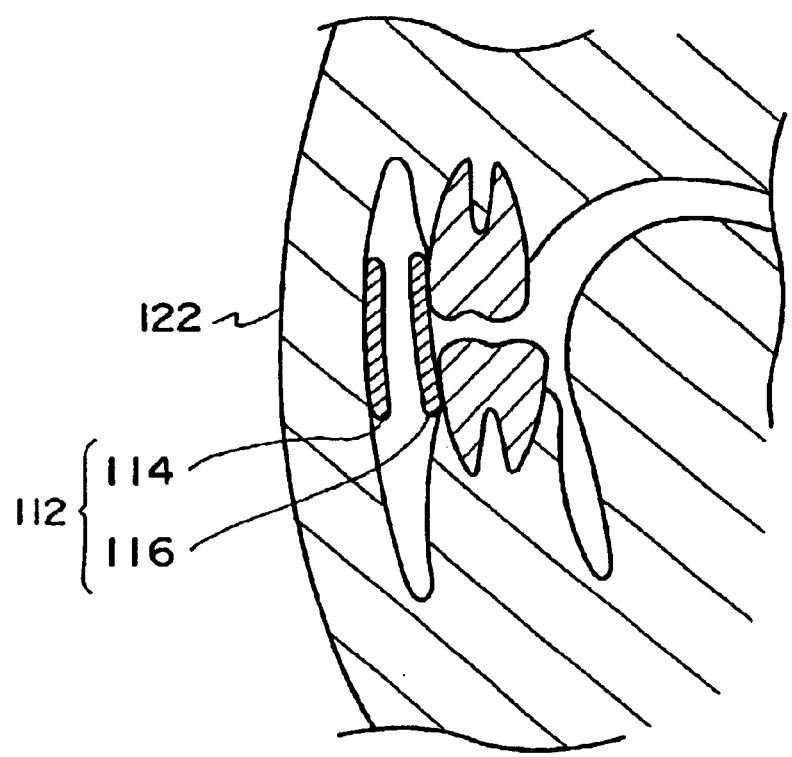
FIG. 15 is a cross-sectional view taken along line 15—15 of FIG. 14 showing a state in which the pressure of the buccinator muscle is being measured using the muscle pressure measuring device for a mouth according to the sixth embodiment of the present invention.

As shown in FIGS. 14 and 15, the muscle pressure measuring device 110 for a mouth of the present embodiment has mounted thereto mouthpieces 112 for measuring the pressure of the buccinator muscle abutting the group of the side teeth (such as the canine tooth, the bicuspid tooth, and the molar tooth).

The mouthpieces 112 for the side tooth group include an outer mouthpiece 114 and an inner mouthpiece 116.

In the present embodiment, as shown in FIG. 14, the outer mouthpiece 114 is connected to the shaft 26 of the force measuring device 11, while the inner mouthpiece 116 is connected to the mouthpiece-mounting bracket 38.

A connecting shaft 118 of the outer mouthpiece 114 is connected to the shaft 26 of the force measuring device 11, and a connecting shaft 120 of the inner mouthpiece 116 is connected to the mouthpiece-mounting bracket 38 of the force measuring device 11.

The connecting shafts 118 and 120 respectively have a portion curved along the tooth row and are bent near the front teeth so as to extend to the outside of the mouth.

Further, the outer mouthpiece 114 and the inner mouthpiece 116 are curved so as to conform to the curvature of the side tooth group.

Next, usage of the muscle pressure measuring device 110 of the present embodiment will be described.

(1) First, the mouthpieces 112 are disposed in the mouth between a cheek 122 and the side tooth group. Moreover, the inner mouthpiece 116 is slightly pressed against the side tooth group so as not to be moved.

(2) When the examinee closes his/her lips in this state, the inner mouthpiece 116 and the outer mouthpiece 114 are nipped between the cheek 122 and the side tooth group, and the shaft 26 of the force measuring device 11 is pressed towards the side tooth group side by the cheek 122.

The force acting on the shaft 26 is the pressure of the buccinator muscle. The amount of the force acting on the shaft 26, namely, the amount of the pressure of the buccinator muscle, is digitally displayed on the display 36.

The mouthpieces 112 of different sizes and lengths are often prepared, such as large mouthpieces for adults and small mouthpieces for children.

[Seventh Embodiment]

A muscle pressure measuring device 130 for a mouth according to a seventh embodiment of the present invention will be described with reference to FIGS. 16A and 16B. Components of the device of the present embodiment which are similar to those of the devices of the above-described embodiments are designated by the same reference numerals, and detailed description thereof will be omitted.

Figure 16A:
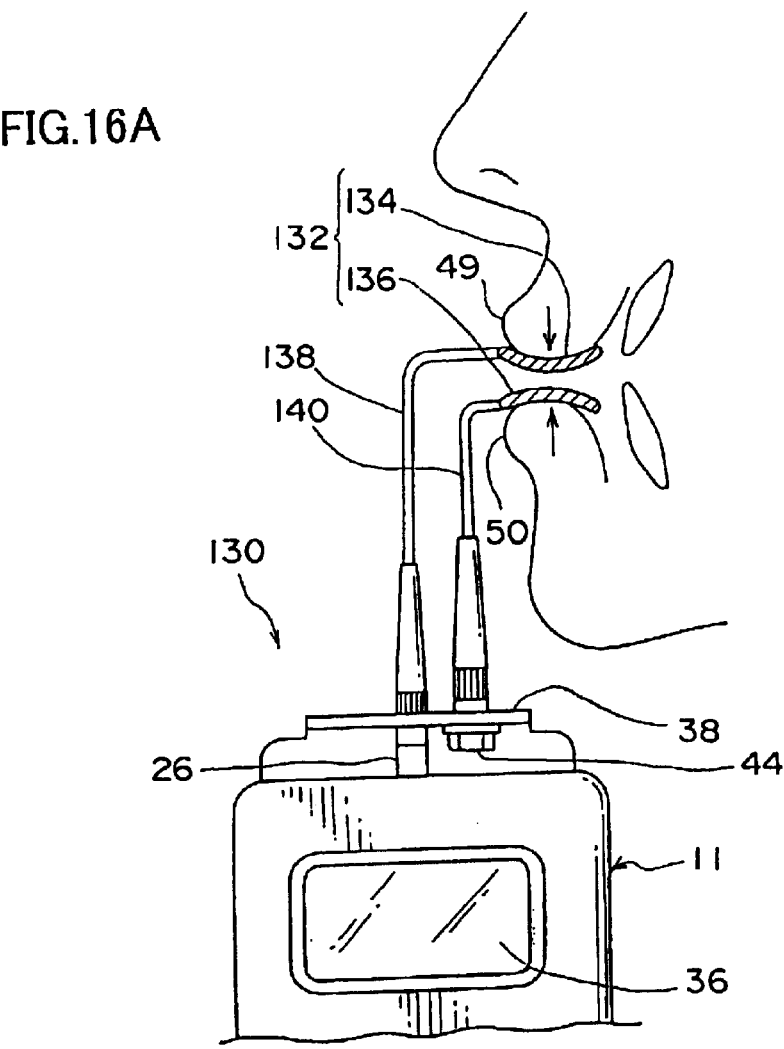
FIG. 16A is a side view showing a state in which closing force of upper and lower lips is being measured using a muscle pressure measuring device for a mouth according to a seventh embodiment of the present invention.
Figure 16B:
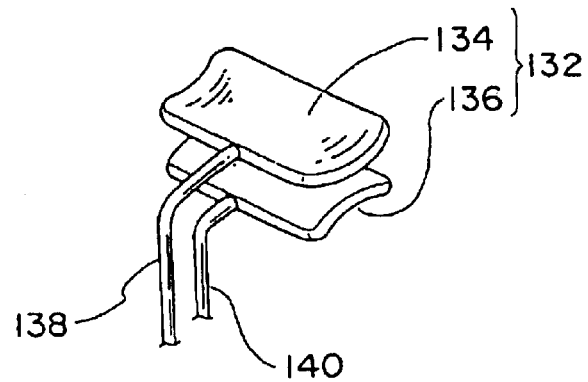
FIG. 16B is a perspective view of mouthpieces.

FIG. 16A is a side view showing a state in which closing force (pressure) of the upper and lower lips is being measured using the muscle pressure measuring device 130 for a mouth.

As shown in FIG. 16, the muscle pressure measuring device 130 for a mouth of the present embodiment has mounted thereto mouthpieces 132 for measuring the closing force or pressure of the upper and lower lips.

The mouthpieces 132 include an upper mouthpiece 134 and a lower mouthpiece 136.

The upper mouthpiece 134 is connected to the shaft 26 of the force measuring device 11, while the lower mouthpiece 136 is connected to the mouthpiece-mounting bracket 38.

A connecting shaft 138 of the upper mouthpiece 134 is connected to the shaft 26 of the force measuring device 11, and a connecting shaft 140 of the lower mouthpiece 136 is connected to the mouthpiece-mounting bracket 38 of the force measuring device 11.

The connecting shafts 138 and 140 are bent so as to be substantially L-shaped.

Further, the upper mouthpiece 134 and the lower mouthpiece 136 are curved so as to conform to the shape of the lips.

Next, usage of the muscle pressure measuring device 130 for a mouth of the present embodiment will be described.

When the mouthpieces 132 are disposed between the upper lip and the lower lip, and the upper lip 49 and the lower lip 50 are closed, the upper mouthpiece 134 and the lower mouthpiece 136 are nipped by the upper lip 49 and the lower lip 50. The amount of the force acting on the shaft 26, i.e., the amount of the closing force (pressure) of the upper and lower lips is digitally displayed on the display 36.

In the present embodiment, the closing force (pressure) of the upper and lower lips is measured using the muscle pressure measuring device 130 for a mouth. However, masticatory force (strength of a masseter) can also be measured when the upper mouthpiece 134 and the lower mouthpiece 136 are disposed between the tooth row in the upper jaw and the tooth row in the lower jaw so as to be bitten thereby. In this case, it is preferable that the upper mouthpiece 134 and the lower mouthpiece 136 are plate-shaped rather than curved, and respectively have a sheet of an elastic material such as rubber attached thereto at a portion abutting the tips of the teeth.

Further, the masticatory force is very large in comparison with the closing force of the upper and lower lips. Therefore, when masticatory force is measured, the connecting shafts 138 and 140 and the like need to be thickened so as not to be bendable.

What is claimed is:

1. A muscle pressure measuring device for measuring the pressure exerted by a body part within a mouth including at least one of an upper or lower lip, a muscle around an oral cavity, a buccinator muscle, and a tongue, comprising:

a pair of mouthpieces each having an interior surface and an exterior surface, the interior surfaces facing each other, wherein the interior surfaces move toward each other under the influence of pressure exerted on at least one of the exterior surfaces by the body part; and a force measuring device connected to the pair of mouthpieces for measuring force acting on the exterior surface of the mouthpieces as the pressure when the interior surfaces of the mouthpieces approach each other.

2. The muscle pressure measuring device for a mouth of claim 1, wherein the pair of mouthpieces are curved along a tooth row.

3. The muscle pressure measuring device for a mouth of claim 1, wherein the pair of mouthpieces are removable with respect to the force measuring device.

4. The muscle pressure measuring device for a mouth claim 1, wherein a gap between the pair of mouthpieces becomes smaller towards the base of gum when the pair of mouthpieces are disposed along the tooth row.

5. The muscle pressure measuring device for a mouth of claim 1, wherein the mouthpiece is formed of at least one material selected from stainless steel, ceramic, and synthetic resin.

6. The muscle pressure measuring device for a mouth of claim 1, wherein the pair of mouthpieces are formed by an upper mouthpiece abutting the upper lip and a lower mouthpiece abutting the lower lip.

7. The muscle pressure measuring device for a mount of claim 1, comprising a plurality of mouthpieces of different configurations, which mouthpieces are formed based on an average size of a dental arch of normal occlusion of each age group.

8. The muscle pressure measuring device for a mouth of any one of claim 1, wherein a recess for avoiding contact with a frenulum of the upper or lower lip is provided in a center of each of the pair of mouthpieces.

9. The muscle pressure measuring device for a mouth of claim 1, wherein the mouthpiece includes an elastic body covering at at least a portion of the exterior surface in contact with a tooth.

10. The muscle pressure measuring device for a mouth of claim 6, wherein the upper mouthpiece and the lower mouthpiece are removable with respect to the force measuring device.

11. The muscle pressure measuring device for a mouth of claim 6, wherein the upper mouthpiece and the lower mouthpiece are formed of at least one material selected from metals including stainless steel, ceramic, and synthetic resin.

12. The muscle pressure measuring device for a mouth of claim 9, wherein the elastic body is removable attached to the exterior surface mouthpiece.

13. The muscle pressure measuring device for a mouth of claim 9, wherein the mouthpiece is formed of metal.

14. The muscle pressure measuring device of claim 1, wherein each of the pair of mouthpieces is provided at an end of each of a pair of shafts, and another end of said each of the pair of shafts is connected to the force measuring device.

15. The muscle pressure measuring device of claim 14, wherein one of the pair of shafts is connected to a main body of the force measuring device, and another of the pair of shafts is connected to a force measuring portion of the force measuring device.

16. The muscle pressure measuring device of claim 1, wherein a notch is formed in a center of an edge of each of the pair of mouthpieces.

17. The muscle pressure measuring device of claim 1, wherein an elastic portion is provided at the portion to be subjected to pressure by the body part to be measured.

18. A muscle pressure measuring device for a mouth, comprising:
  a mouthpiece disposed in a mouth along a tooth row, the mouthpiece comprising a plurality of fluid chambers along the tooth row, the plurality of fluid chambers being filled with a fluid and whose wall surfaces are made of a flexible material; and
  a pressure measuring device which is connected via tubes, each tube is connected to one of the fluid ehember chambers, in order to measure pressure on the fluids inside the fluid chambers.

19. An adapter for a muscle pressure measuring device to measure the pressure exerted by a body part within a mouth including at least one of an upper or lower lip, a muscle around an oral cavity, a buccinator muscle, and a tongue, comprising:
  a first member having a first connecting portion connected to a main body of a force measuring device, and a first mouthpiece having a an exterior surface and a contacting portion opposite to the first connecting portion, the contacting portion engageable with the body part to be measured; and
  a second member having a second connecting portion connected to a main body of a force measuring device, and a second mouthpiece having a an exterior surface and a contacting portion opposite to the second connecting portion, the contacting portion engageable with the body part to be measured,
  wherein, when the first connecting portion is connected to the main body and the second connecting portion is connected to the force measuring portion, the first mouthpiece and the second mouthpiece face each other and can be subjected to pressure by the body part to be measured in a direction closer towards each other.

* * * * *